United States Patent [19]

Gleason et al.

[11] Patent Number: 4,775,662

[45] Date of Patent: Oct. 4, 1988

[54] LEUKOTRIENE ANTAGONISTS

[75] Inventors: John G. Gleason, Delran, N.J.; Thomas W. Ku, Dresher, Pa.

[73] Assignee: SmithKline Beckman Corporation, Philadelphia, Pa.

[21] Appl. No.: 114,820

[22] Filed: Oct. 29, 1987

Related U.S. Application Data

[63] Continuation of Ser. No. 000,783, Jan. 6, 1987, abandoned, which is a continuation of Ser. No. 761,729, Aug. 2, 1985, abandoned, which is a continuation of Ser. No. 472,773, Mar. 7, 1983, abandoned.

[51] Int. Cl.⁴ .................. C07C 149/20; A61K 31/195
[52] U.S. Cl. ........................... 514/19; 514/562; 514/574; 514/616; 562/556; 562/557; 562/581; 562/594; 564/153; 564/154
[58] Field of Search ............... 562/556, 557, 581, 594; 564/153, 154; 260/399, 402.5; 514/19, 547, 549, 560, 562, 616, 574

[56] References Cited

U.S. PATENT DOCUMENTS

| | | | |
|---|---|---|---|
| 4,176,235 | 11/1979 | Ondetti | 562/556 |
| 4,177,277 | 12/1979 | Ondetti | 562/566 |
| 4,297,275 | 10/1981 | Sundeen | 260/112.5 R |
| 4,461,775 | 7/1984 | Stanley | 424/311 |
| 4,469,705 | 9/1984 | Stanley | 424/312 |
| 4,513,005 | 4/1985 | Baker | 514/451 |

FOREIGN PATENT DOCUMENTS 0068739 1/1983 European Pat. Off. .

OTHER PUBLICATIONS

Derwent Patent Abstract Bulletin (73260E).
Allinger, "Organic Chemistry", p. 458 (1971).
Drazen, Proc. Natl. Acad. Sc., 78 pp. 3195–3198 (1981).
Derwent Patent Abstract No. 73251 E/35 (1982).

Primary Examiner—Michael L. Shippen
Attorney, Agent, or Firm—Nancy S. Mayer; Janice E. Williams; Alan D. Lourie

[57] ABSTRACT

The compounds represented by the formula (I)

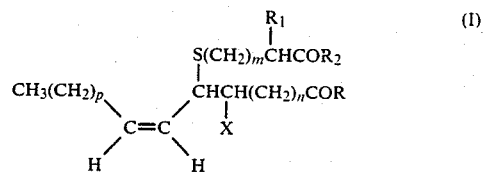

wherein n is 1 or 2; m is 0, 1 or 2; p is 9, 10, 11, 12 or 13; X is hydrogen or hydroxyl; R is hydroxyl or amino; $R_1$ is hydrogen, amino or

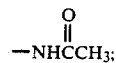

and $R_2$ is hydroxyl, amino,

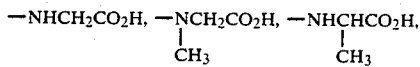

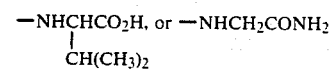

with the proviso that when m is 0, $R_1$ is hydrogen or pharmaceutically acceptable salts thereof have been found to be leukotriene antagonists and useful in the treatment of diseases in which leukotrienes are a factor, such as asthma.

32 Claims, No Drawings

LEUKOTRIENE ANTAGONISTS

This is a continuation of application Ser. No. 000,783 filed Jan. 6, 1987, now abandoned, which is a continuation of application Ser. No. 761,729 filed Aug. 2, 1985, now abandoned, which is a continuation of application Ser. No. 472,773 filed Mar. 7, 1983, now abandoned.

BACKGROUND OF THE INVENTION

"Slow Reacting Substance of Anaphylaxis" (SRS-A) has been shown to be a highly potent broncho-constricting substance which is released primarily from mast cells and basophils on antigenic challenge. SRS-A has been proposed as a primary mediator in human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$, ($LTD_4$) and leukotriene-$E_4$, ($LTE_4$); the structural formulae of which are represented below.

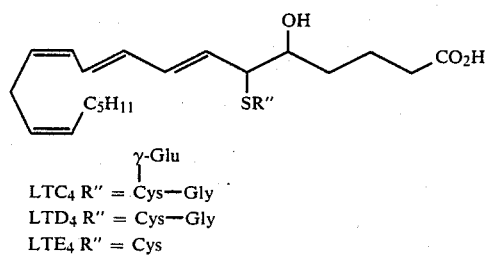

$LTC_4$ R″ = Cys—Gly  γ-Glu
$LTD_4$ R″ = Cys—Gly
$LTE_4$ R″ = Cys

By antagonizing the effects of $LTC_4$, $LTD_4$ and $LTE_4$ or other pharmacologically active mediators at the end organ, airway smooth muscle, the compounds and pharmaceutical compositions of the instant invention are valuable in the treatment of diseases in which leukotrienes are a factor, such as asthma.

DETAILED DESCRIPTION OF THE INVENTION

The compounds of this invention are represented by the following general structural formula (I)

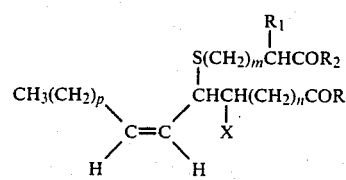

wherein n is 1 or 2; m is 0, 1 or 2; p is 9, 10, 11, 12 or 13; X is hydrogen or hydroxyl; R is hydroxyl or amino; $R_1$ is hydrogen, amino or

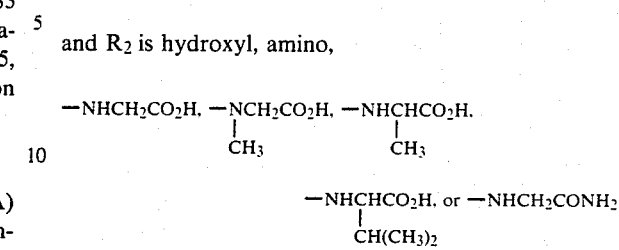

and $R_2$ is hydroxyl, amino, $$-NHCH_2CO_2H, -NCH_2CO_2H, -NHCHCO_2H,$$
$$\phantom{-NHCH_2CO_2H, -N}| \phantom{CH_2CO_2H, -NHCH}|$$
$$\phantom{-NHCH_2CO_2H, -NCH_2CO_2H,} CH_3 \phantom{-NHCH} CH_3$$

$$-NHCHCO_2H, \text{ or } -NHCH_2CONH_2$$
$$\phantom{-NHCH}|$$
$$\phantom{-NHCH}CH(CH_3)_2$$

with the proviso that when m is 0, $R_1$ is hydrogen or a pharmaceutically acceptable salt thereof.

The stereochemistry of the compounds of formula (I) is such that the double bond adjacent to the alkyl moiety is in the cis configuration. The compounds of formula (I) are the result of a Wittig reaction between appropriate alkyltriphenyl phosphonium ylid with an appropriate intermediate compound. The compounds of formula (I) wherein n is 2 and p is 11 have a $C_{19}$ carbon skeleton and are designated 6(Z)-nonadecenoic acid derivatives. Similarly, when n is 1 and p is 11, the compounds of formula (I) have a $C_{18}$ carbon skeleton and are designated 5(Z)-octadecenoic acid derivatives. When n is 2 and p is 9 the compounds of formula (I) have a $C_{17}$ carbon skeleton and are designated 6(Z)-heptadecenoic acid derivatives. Also, when n is 2 and p is 13 the compounds of formula (I) have a $C_{21}$ carbon skeleton and are designated 6(Z)-heneicosenoic acid derivatives.

The 6(Z)-nonadecenoic acid derivatives of the compounds of formula (I) wherein R is hydroxyl and X is hydroxyl are represented by the following general structural formula (II)

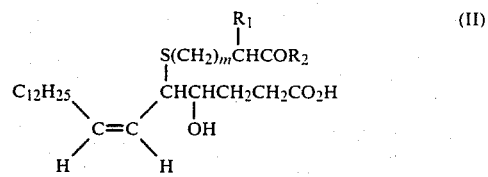

wherein m, $R_1$ and $R_2$ are described above. The compounds of the formula (II) contain two asymmetric centers, one of which is at carbon atom 4 (i.e. the hydroxyl substituted carbon atom-"$C_4$") and one of which is at carbon atom 5 (i.e. the thiol substituted carbon atom-"$C_5$"). This leads to the possibility of four stereoisomers for each compound. In practice, the compounds of this invention of formula (II) have been prepared in a mixture of two stereoisomers, that is the 4R, 5S isomer and the 4S, 5R isomer. The individual pure stereoisomers are obtainable by preparative high pressure liquid chromatography (HPLC) separation of the appropriate intermediate compounds if those compounds possess a third asymmetric center. In the cases where a third asymmetric center is not available in the synthetic pathway of the desired compounds, one may be introduced by employing an asymmetric protecting group, such as an N-trifluoroethoxycarbonyl-i-prolyl ester. After separation of the individual stereoisomer, the protecting group is removed by standard procedures.

The 6(Z)-nonadecenoic acid derivatives of formula (II) are exemplified by the following compounds as the 4R, 5S isomer, the 4S, 5R isomer or mixture of the two isomers:

4-hydroxy-5-[(2-carboxyethyl)thio]-6(Z)-nonadecenoic acid, wherein m is 1, $R_1$ is hydrogen and $R_2$ is hydroxyl;

5-[(3-carboxymethylamino-3-oxopropyl)thio]-4-hydroxy-6(Z)-nonadecenoic acid, wherein m is 1, $R_1$ is hydrogen and $R_2$ is —NHCH$_2$CO$_2$H;

5-[(2-amino-3-carboxymethylamino-3-oxopropyl)thio]-4-hydroxy-6(Z)-nonadecenoic acid, wherein m is 1, $R_1$ is amino and $R_2$ is —NHCH$_2$CO$_2$H;

5-[(3-carboxymethyl-N-methylamino-3-oxopropyl)thio]-4-hydroxy-6(Z)-nondecenoic acid, wherein m is 1, $R_1$ is hydrogen and $R_2$ is

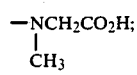

5-[(2-amino-3-carboxamidomethylamino-3-oxopropyl)-thio]-4-hydroxy-6(Z)-nonadecenoic acid, wherein m is 1, $R_1$ is amino and $R_2$ is —NHCH$_2$CONH$_2$;

4-hydroxy-5-[(carboxymethyl)thio]-6(Z)-nonadecenoic acid, wherein m is 0, $R_1$ is hydrogen and $R_2$ is hydroxyl;

5-[[2-(aminocarbonyl)ethyl]thio]-4-hydroxy-6(Z)-nonadecenoic acid, wherein m is 1, $R_1$ is hydrogen and $R_2$ is amino;

4-hydroxy-5-[(2-amino-2-carboxyethyl)thio]-6(Z)-nonadecenoic acid, wherein m is 1, $R_1$ is amino and $R_2$ is hydroxyl; and 4-hydroxy-5-[(3-carboxypropyl)thio]-6(Z)-nonadecenoic acid, wherein m is 2, $R_1$ is hydrogen and $R_2$ is hydroxyl.

The 5(Z)-octadecenoic acid derivatives of the compounds of formula (I) wherein R is hydroxyl are represented by the following general structural formula (III)

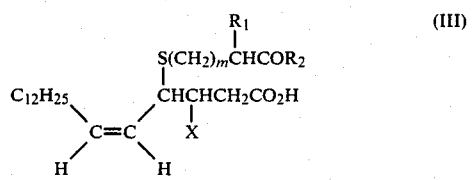

wherein m, X, $R_1$ and $R_2$ are described above. Like the 6(Z)-nonadecenoic acid derivatives of formula (II), the 5(Z)-octadecenoic acid derivatives contain two asymmetric centers at carbon atoms $C_3$ and $C_4$ and thus the possibility of four stereoisomers for each compound exists.

Specific compounds of the formula (III) are those 5(Z)-octadecenoic acid derivatives exemplified by the following compounds as a mixture of the four isomers:

3-hydroxy-4-[(2-carboxyethyl)thio]-5(Z)-octadecenoic acid, wherein m is 1, X is hydroxyl, $R_1$ is hydrogen and $R_2$ is hydroxyl.

Also representative of the compounds of formula (III) is 4-[(2-carboxyethyl)thio]-5(Z)-octadecenoic acid, wherein m is 1, X is hydrogen, $R_1$ is hydrogen and $R_2$ is hydroxy.

The compounds of the formula (I) wherein X is hydrogen are represented by the general structural formula (IV):

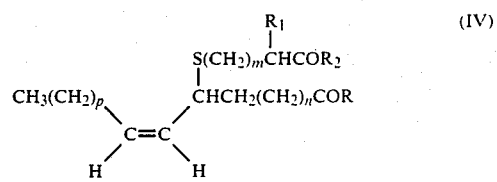

wherein n, m, p, R, $R_1$ and $R_2$ are described above. Specific compounds of formula (IV) are those 6(Z)-nonadecenoic acid derivatives wherein n is 2 p is 11 and R is hydroxyl which are exemplified by the following compound:

5-[(2-carboxyethyl)thio]-6(Z)-nonadecenoic acid, wherein m is 1, $R_1$ is hydrogen and $R_2$ is hydroxyl.

Specific compounds of the formula (I) are those 6(Z)-nonadecenoic acid derivatives wherein R is amino and X is hydroxyl which are represented by the general formula (V) as follows:

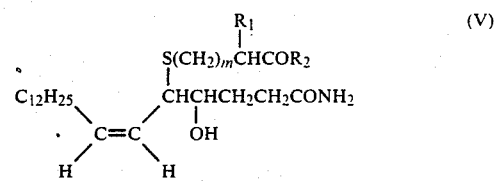

wherein m, $R_1$ and $R_2$ are described above. The 6(Z)-nonadecenoic acid derivatives of formula (V) are exemplified by the following compounds as a mixture of isomers:

5-[(3-carboxymethylamino-3-oxopropyl)thio]-4-hydroxy-6(Z)-nonadecenamide, wherein m is 1, $R_1$ is amino and $R_2$ is —NHCH$_2$CO$_2$H; and 4-hydroxy-5-[(2-carboxyethyl)thio]-6(Z)-non-adecenamide, wherein m is 1; $R_1$ is hydrogen and $R_2$ is hydroxyl.

Additional compounds of the formula (I) are those 6(Z)-heptadecenoic acid derivatives wherein R is hydroxyl and X is hydroxyl which are represented by the general structural formula (VI) as follows:

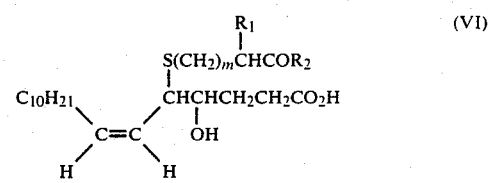

wherein m, $R_1$ and $R_2$ are described above. The 6(Z)-heptadecenoic acid derivatives of formula (VI) are exemplified as a mixture of isomers:

4-hydroxy-5-[(2-carboxyethyl)thio]-6(Z)-heptadecenoic acid, wherein m is 1, $R_1$ is hydrogen and $R_2$ is hydroxyl.

Further compounds of the formula (I) are those 6(Z)-heneicosenoic acid derivatives wherein R is hydroxyl and X is hydroxyl which are represented by the general structural formula (VII) as follows:

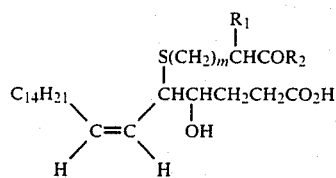

wherein m, $R_1$ and $R_2$ are described above. The 6(Z)-heneicosenoic acid derivatives of the formula (VII) are exemplified as a mixture of isomers:

4-hydroxy-5-[(2-carboxyethyl)thio]-6(Z)-heneicosenoic acid, wherein m is 1, $R_1$ is hydrogen and $R_2$ is hydroxyl.

The compounds of the formula (II) are readily prepared by reacting the appropriate thiol containing compound of the formula (A)

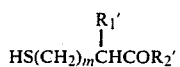

wherein m is described above and $R_1'$ and $R_2'$ are respectively $R_1$ and $R_2$ or a protecting radical easily convertible to the desired substituent, such as an alkyl ester or trifluoromethylacetamide, with a 4,5-epoxy-6(Z)-nonadecenoic acid derivative of the formula (B)

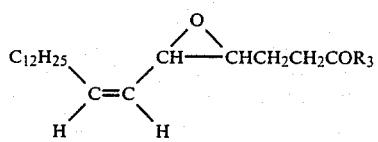

wherein —$COR_3$ is a radical which is easily convertible into the desired acid moieties, such as $CO_2$alk wherein alk is a lower alkyl group. The thiol containing compounds of formula (A) are known or easily prepared from known compound utilizing standard chemical transformations. The 4,5-epoxy-6(Z)-nonadecenoic acid derivatives (B) are readily prepared from monoalkyl succinate (1) via the following synthetic pathway:

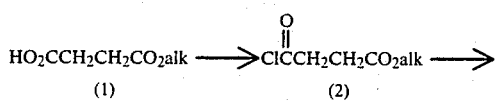

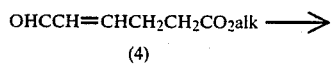

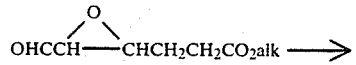

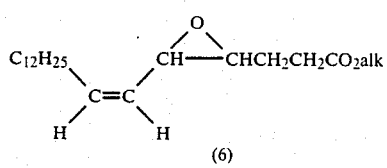

Mono-methyl succinate (1), wherein alk is methyl, was chlorinated with oxalyl chloride in dimethyl formamide and methylene chloride to afford 3-carbomethoxypropionyl chloride (2). Compound (2) was catalytically hydrogenated over palladium-charcoal catalyst in the presence of 2,6-lutidine to yield 3-carbomethoxypropionaldehyde (3) which was reacted with formylmethylene triphenylphosphorane under Wittig reaction conditions to obtain 5-carbomethoxy-2-pentanal (4). Compound 4 was epoxidized with aqueous hydrogen peroxide in the presence of 1N sodium bicarbonate to afford methyl-4,5-epoxy-6-oxohexanoate (5). Compound (5) was reacted with tridecyltriphenylphosphonium ylid to give methyl-4,5-epoxy-6(Z)-nonadecenoate (6).

The 5(Z)-octadecenoic acid derivatives of the formula (III) wherein X is hydroxy are prepared via the synthetic pathway starting from 2(E),4(Z)-heptadecadienol (7) as follows:

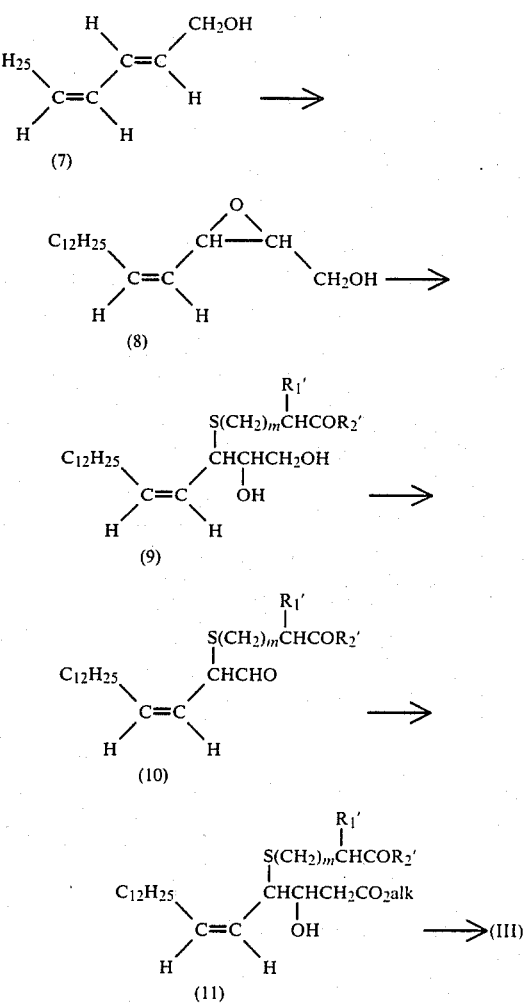

Compound (7) was reacted with m-chloroperbenzoic acid (MCPBA) to afford 2,3-trans-epoxy-4(Z)-heptadecenol (8). Compound 8 was reacted with methyl-3-mercaptopropionate (m=1, $R_1'$=H and $R_2'$=—$OCH_3$) to yield 3-[(2-carbomethoxyethyl)thio]-1,2-dihydroxy-4(Z)-heptadecane (9). The 1,2-diol moiety of Compound (9) was cleaved by periodate to give 2-[(2-carbomethoxyethyl)thio]-3(Z)-hexadecenal (10). Compound (10) was reacted with methyl acetate (alk=—$OCH_3$) in the presence of lithium diisopropylamide to give methyl-3-hydroxy-4-[(2-carbomethoxyethyl)thio]-5(Z)-octadecenoate (11) which was saponified to afford compound of the formula (III) wherein m is 1, $R_1$ is hydroxyl, $R_1$ is hydrogen and $R_2$ is hydroxyl.

The 6(Z)-nonadecenoic acid derivatives of formula (IV) are prepared via the pathway starting from 5-carboxyalkyl pentanoic acid (12) as follows:

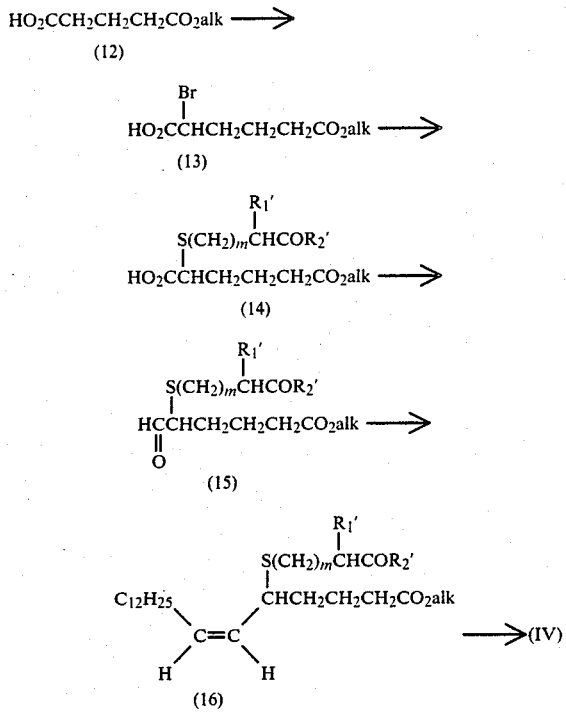

5-Carbomethoxypentanoic acid (12), wherein alk is methyl, was reacted with thionyl chloride and then N-bromosuccinimide (NBS) followed by base hydrolysis to give 2-bromo-5-carbomethoxypentanoic acid (13). Compound (13) was reacted with methyl-3-mercaptopropionate (m=1, $R_1'$=H and $R_2'$=OCH$_3$) to yield 5-carbomethoxy-2-[(2-carbomethoxyethyl)thio]-pentanoic acid (14). Compound (14) reacted first with diborane and then with dimethylsulfoxide and trifluoroacetic anhydride to afford 5-carbomethoxy-2-[(2-carbomethoxyethyl)thio]-pentanal (15). Compound (15) was reacted under Wittig conditions with tridecyltriphenylphosphonium ylid to yield methyl-5-[(2-carbomethoxyethyl)thio]-6(Z)-nonadecenoate (16) which was saponified to afford a compound of the formula (IV) wherein m is 1, $R_1$ is hydrogen, and $R_2$ is hydroxyl.

The 5(Z)-octadecenoic acid derivatives of the formula (III) wherein X is hydrogen can be prepared via the general synthetic pathway utilized for the preparation of the 6(Z)-nonadecenoic acid derivatives of formula (IV) but starting from 4-carboxyalkyl butanoic acid.

The compounds of the formula (V) can be prepared by initially forming the γ-lactone of the appropriate compound of formula (II) with trifluoroacetic anhydride and then reacting the γ-lactone with ammonia to afford the desired amide.

The compounds of formulae (VI) and (VII) are conveniently prepared employing procedures analogous to those utilized in the preparation of compounds of the formula (II) by substituting the appropriate $C_{11}$ and $C_{15}$ alkyl triphenyl phosphonium ylid for the tridecyltriphenyl phosphonium ylid in the reaction with the epoxide aldehyde, compound (5) to obtain intermediate compounds of the structural formula (C) as follows:

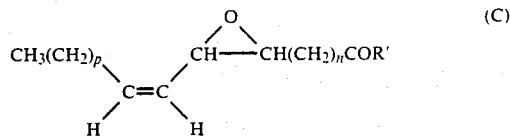

wherein n and p are described above and R' is R or a protecting radical easily convertible to R such as, —Oalk wherein alk is an alkyl radical containing one to six carbon atoms.

The instant invention also includes the compounds of formula (C) above which possess the double bond in the cis conformation. The structural similarities between the compounds of formula (C) and the compounds of formula (I) contribute the leukotriene antagonist properties of the compounds of formula (I).

The leukotriene antagonist activity of the compounds of this invention is measured by the ability of the compound to inhibit leukotriene induced contraction of guinea pig tracheal tissues in vitro and to inhibit leukotriene induced bronchoconstriction in guinea pigs in vivo. The following methodologies were employed:

In vitro: Guinea pig (adult male albino Hartley strain) tracheal spiral strips of approximate dimensions 2 to 3 mm cross-sectional width and 3.5 cm length were bathed in modified Krebs buffer in jacketed 10 ml tissue bath and continously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1 μM) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$ were standardized as a percentage of the maximum response obtained to a reference agonist, carbachol (10 μM).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The $pA_2$ value for the test compound was determined by the following equations:

$$\frac{EC_{30} \text{ (presence of test compound)}}{EC_{30} \text{ (presence of vehicle control)}} = \text{dose ratio} = X \qquad 1.$$

$$K_B = \text{concentration of test compound}/(X - 1) \qquad 2.$$

$$pA_2 = -\log K_B \qquad 3.$$

In vivo: Anesthetized, spontaneously breathing guinea pigs (Adult male albino Hartley strain) were monitored on a Buxco pulmonary mechanics computer. Changes in airway resistance ($R_L$) were calculated by the computer on a breath-by-breath basis at isovolumic points from signals measuring airflow and transpulmonary pressure using differential pressure transducers. Animals received either test compound or vehicle control intravenously via the jugular vein. LTD$_4$ was then injected into the jugular vein. The bronchoconstriction produced was reflected by % changes in airways resistance relative to the baseline values obtained prior to injection of the test compound or vehicle control. Each guinea pig received either vehicle control or test compound.

Calculations: The average of 3-6 animals per treatment was calculated using the % changes in the pulmonary parameters for control and test compound-treated animals. The average % inhibition by the test compound was calculated from the following equation:

$$\frac{R_{L\text{(vehicle control)}} - R_{L\text{(test compound)}}}{R_{L\text{(vehicle control)}}} \times 100$$

The compounds of this invention possess biosignificant antagonist activity against leukotrienes, primarily leukotriene D$_4$. Representative of the antagonist activity of the compounds of this invention, tabulated below are a number of claimed compounds and the pA$_2$ values and the R$_L$ values calculated from the above test protocols.

of leukotrienes, such as symptoms of asthma and other allergic diseases.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspending agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally or by inhalation.

In general, particularly for the prophylactic treatment of asthma, the compositions will be in a form suitable for administration by inhalation. Thus the compositions will comprise a suspension or solution of the active ingredient in water for administration by means

| n | m | p | X | R | R$_1$ | R$_2$ | In Vitro pA$_2$ | In Vitro Concentration | R$_L$ |
|---|---|---|---|---|---|---|---|---|---|
| Compounds of the Formula (II) | | | | | | | | | |
| | 1 | | | | H | —OH | 6.2 | 5 mg/kg | 91% |
| | 1 | | | | H | —NHCH$_2$CO$_2$H | 6.2 | 5 mg/kg | 36% |
| | $^{(a)}$1 | | | | —NH$_2$ | —NHCH$_2$CO$_2$H | 5.2 | 5 mg/kg | 96% |
| | $^{(b)}$1 | | | | —NH$_2$ | —NHCH$_2$CO$_2$H | 5.0$^{(c)}$ | — | — |
| | 1 | | | | H | —N(CH$_3$)CH$_2$CO$_2$H | 6.1 | 5 mg/kg | 90% |
| | 1 | | | | —NH$_2$ | —NHCH$_2$CONH$_2$ | 5.5 | 5 mg/kg | 98% |
| | 0 | | | | H | —OH | 5.9 | — | — |
| | 1 | | | | H | —NH$_2$ | 5.1 | 5 mg/kg | 38% |
| | $^{(a,d)}$1 | | | | —NH$_2$ | —OH | 5.1 | — | — |
| | $^{(b,e)}$1 | | | | —NH$_2$ | —OH | 5.1 | — | — |
| | 2 | | | | H | —OH | 6.2 | 5 mg/kg | 88% |
| Compounds of the Formula (III) | | | | | | | | | |
| | 1 | | OH | H | | —OH | 6.1 | 10 mg/kg | 88% |
| | 1 | | H | H | | —OH | 6.6 ± 0.4 | — | — |
| Compounds of the Formula (IV) | | | | | | | | | |
| 2 | 1 | 11 | OH | H | | OH | 5.5 | 10 mg/kg | 98% |
| Compounds of the Formula (V) | | | | | | | | | |
| | $^{(f)}$1 | | | | —NH$_2$ | —NHCH$_2$CO$_2$H | 4.9 | — | M |
| | $^{(g)}$1 | | | | H | OH | 5.4 | — | — |
| Compounds of the Formula (VI) | | | | | | | | | |
| | 1 | | | | H | —OH | 5.3 | — | — |
| Compounds of the Formula (VII) | | | | | | | | | |
| | 1 | | | | H | —OH | 5.1 | — | — |

$^{(a)}$4(R), 5(S) isomer
$^{(b)}$4(S), 5(R) isomer
$^{(c)}$partial agonist
$^{(d)}$1.0 Na salt
$^{(e)}$1.5 Na salt $^{(f)}$Na Salt
$^{(g)}$0.3 M NH$_3$ The specificity of the antagonist activity of a number of the compounds of this invention is demonstrated by relatively low levels of antagonism toward agonists such as potassium chloride, carbachol, histamine and PGF$_{2\alpha}$.

Pharmaceutical compositions of the present invention comprise a pharmaceutical carrier or diluent and an amount of a compound of the formula (I) or a pharmaceutically acceptable salt, such as an alkali metal salt thereof sufficient to produce the inhibition of the effects of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in less, equal or greater amounts than the solid active ingredient.

For parenteral administration the pharmaceutical composition will be in the form of a sterile injectable liquid such as an ampul or an aqueous or nonaqueous liquid suspension.

Usually a compound of formula I is administered to an animal subject in a composition comprising a nontoxic amount sufficient to produce an inhibition of the symptoms of an allergic response. When employed in this manner, the dosage of the composition is selected from the range of from 350 mg. to 700 mg. of active ingredient for each administration. For convenience, equal doses will be administered 1 to 4 times daily with the daily dosage regimen being selected from about 350 mg. to about 2800 mg.

The pharmaceutical preparations thus described are made following the conventional techniques of the pharmaceutical chemist as appropriate to the desired end product.

Included within the scope of this disclosure is the method of inhibiting the symptoms of an allergic response resulting from a mediator release which comprises administering to an animal subject a therapeutically effective amount for producing said inhibition of a compound of formula I, preferably in the form of a pharmaceutical composition. The administration may be carried out in dosage units at suitable intervals or in single doses as needed. Usually this method will be practiced when relief of allergic symptoms is specifically required, however, the method is also usefully carried out as continuous or prophylactic treatment. It is within the skill of the art to determine by routine experimentation the effective dosage to be administered from the dose range set forth above, taking into consideration such factors as the degree of severity of the allergic condition being treated, and so forth.

The following examples illustrate the preparation of the compounds of this invention and their incorporation into pharmaceutical compositions and as such are not to be considered as limiting the invention set forth in the claims appended hereto.

EXAMPLE 1

Preparation of
5-[(2-amino-3-carboxymethylamino-3-oxopropyl)thio]-4-hydroxy-6(Z)-nonadecenoic acid [Formula (II) wherein m is 1, $R_1$ is amino and $R_2$ is —NHCH$_2$CO$_2$H] as the 4(R),5(S) isomer, 4(S),5(R) isomer and the mixture of the two isomers (a)

3-Carbomethoxypropionyl chloride 1(a)

To an ice-cold solution of mono-methyl succinate, (150 g, 1.135 mol) in 900 ml of methylene chloride and 3 ml of N,N-dimethylformamide was added 119 ml (1.26 mol) of oxalyl chloride, while keeping the pot temperature below 5° C. After the addition was complete, the reaction mixture was stirred at 0° C. for 1 hour and then concentrated to vacuo to give a crude yellow liquid, which was used without purification in the Rosenmund reduction.

(b)

3-Carbomethoxypropionaldehyde 1(b)

To the acid chloride, 1(a) (8.9 g, 0.059 mol) in 200 ml of sieve-dried tetrahydrofuran was added 6.9 ml (0.059 mol) of 2,6-lutidine. After standing at room temperature for 30 minutes, the mixture was filtered and 0.7 g of 10% palladium on carbon was added to the filtrate. The mixture was hydrogenated at 50 psi for 2 hours, the solids were filtered off and the filtrate concentrated. The residue was dissolved in methylene chloride, washed twice with 10% hydrochloric acid solution and then twice with 5% sodium bicarbonate solution. The organic extract was dried with anhydrous sodium sulfate and concentrated in vacuo. Kugelrohr distillation (40°-55° C./0.05 mm) yielded a colorless liquid.

(c)

5-Carbomethoxy-2-pentenal 1(c)

To a mechanically-stirred solution of 1(b) (72.1 g, 0.620 mol) in 750 ml of toluene under argon was added 235.9 g (0.776 mol) of formylmethylene triphenylphosphorane. The reaction mixture was refluxed for 1.5 hours, cooled to room temperature and then concentrated in vacuo. The residue was left standing under diethyl ether at 0° C. overnight. The mixture was filtered and the solid was washed with cold ether. The filtrate was concentrated and the resulting maroon oil was subjected to Kugelrohr distillation. The product was collected at 65°-80° C./0.05 mm.

(d)

Methyl 4,5-Epoxy-6-oxohexanoate 1(d)

To a solution of 36.4 ml of a 30% hydrogen peroxide solution and 58.2 ml of 1N sodium bicarbonate in 800 ml of methanol and 400 ml of water under argon was added dropwise over 45 minutes 41.2 g (0.29 mol) of 1(c) in 400 ml of methanol. After the addition was complete, the reaction was stirred for 2.5 hours at room temperature, while maintaining the pH between 9 and 9.5 by the addition of sodium bicarbonate solution. The reaction mixture was then poured into one liter of saturated ammonium sulfate solution, the methanol was removed in vacuo, the solids were filtered off and the product was extracted into methylene chloride. The aqueous layer was back extracted twice, the combined extracts were dried with anhydrous sodium sulfate and then concentrated to give a crude golden oil. The product was Kugelrohr distilled at 82°-9° C./0.1 mm.

(e)

Methyl 4,5-epoxy-6(Z)-nonadecenoate 1(e)

To an ice-cold solution of tridecyl triphenylphosponuim bromide (preparation described below) (97.2 g, 0.185 mol) in 600 ml of sieve-dried tetrahydrofuran under argon was added dropwise 17.1 ml of a 2.4M solution of n-butyl lithium in hexane; the temperature was maintained at 0° C. during the 30 minute addition. The reaction mixture was stirred at this temperature for an additional 15 minutes, cooled to −78° C. (dry ice/isopropanol) and then 26.5 g (0.168 mol) of 1(d) in 150 ml of dried tetrahydrofuran was added dropwise over 30 minutes. After the addition was complete, the reaction was stirred for 1 hour at −78° C. and then concentrated in vacuo at 24° C. The residue was triturated with hexane and then left standing at 0° C. overnight. The hexane was decanted and then the residue was sonicated four times with hexane. The combined extracts were concentrated in vacuo and the crude product purified by preparative HPLC (2 Waters Prepak silica columns, eluting with 8% ethyl acetate in hexane), giving 1(e) as an oil.

(f)

Tridecyl triphenyl phosphonium bromide

A solution of 1-bromotridecane (100 g, 0.4 mol) and triphenyl phosphine (100 g, 0.4 mol) in 500 ml of xylenes was refluxed overnight. The reaction mixture was then cooled to room temperature and poured into diethyl ether. The resulting oil was washed three times with ether, dissolved in methylene chloride and then concentrated in vacuo. The oil was left standing in diethyl ether at 0° C. overnight and then concentrated in vacuo to give a white solid.

(g)

4-Hydroxy-5-[(2-trifluoroacetamido-3-carbomethoxymethylamino-3-oxopropyl)thio]-6(Z)-nonadecenoic acid, γ-lactone and methyl ester To the epoxide, 1(e) (12.9 g, 0.04 mol) under argon at room temperature was added dropwise over 1 hour a solution of 14.5 g (0.05 mol) of 2-trifluoroacetamido-3-carbomethoxymethylamino-3-oxopropylmercaptan

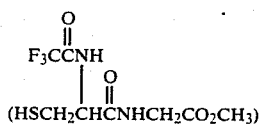

in triethylamine (6.7 ml)/methanol (150 ml). The reaction mixture was stirred at room temperature overnight and then concentrated in vacuo. The residue was dissolved in a minimum volume of methylene chloride, 100 ml. of hexane was added and then this solution was stored at −15° C. for 1 hour. The resulting solid was filtered off and then the filtrated was concentrated in vacuo, to give a crude oil, consisting of a mixture of the desired products.

(h)

4(R)-Hydroxy-5(S)-[(2-trifluoroacetamido-3-carbomethoxymethylamino-3-oxopropyl)thio]-6(Z)-nonadecenoic acid γ-lactone and 4(S)-Hydroxy-5(R)-[(2-trifluoroacetamido-3-carbomethoxymethylamino-3-oxopropyl)thio]-6(Z)-nonadecenoic acid, γ-lactone The crude mixture from Example 1(g) (20.4 g.) in 200 ml of toluene was heated to 80° C. in the presence of 75 mg of p-toluenesulfonic acid for 15 minutes. The reaction mixture was then concentrated in vacuo and the resulting crude oil was purified by preparative HPLC (2Waters Prepak silica columns, eluting with 45% ethyl acetate in hexane) to give the desired products as the pure 4(R), b 5(S) isomer and the pure 4(S), 5(R) isomer.

(i)

4(R)-Hydroxy-5(S)-[(2-amino-3-carboxymethylamino-3-oxopropyl)thio]-6(Z)-nonadecenoic acid, hydrate The lactone of Example 1(h) in the 4(R), 5(S) isomer form, (1.9 g, 0.00327 mol) in aqueous sodium hydroxide (0.72 g, 0.018 mol in 50 ml water) was stirred at room temperature overnight. The pH of the reaction mixture was then adjusted to 3.5 with concentrated hydrochloric acid and the resulting solid was collected and dried: mp 144°–146° C.; Anal. Calcd. for $C_{24}H_{44}N_2O_6S$ $1\frac{1}{4}H_2O$: C, 56.38; H, 9.17; N, 5.48. Found: C, 56.16; H, 8.83; N, 5.54.

Similarly, the lactone of Example 1(h) in the 4(S), 5(R) isomer form was converted to the desired 4(S), 5(R) isomer of the above noted compound: mp 141°–143° C.; Anal. Calcd. for $C_{24}H_{44}N_2O_6S$. $1\frac{1}{4}H_2O$: C, 56.39; H, 9.17; N, 5.48; Found: C, 56.20; H, 8.88; N, 5.18.

The isomeric mixture of the desired product was obtained treating the mixture of products prepared according to Example 1(g) without separation as described above: mp 140°–143° C.; Anal. Calcd for $C_{24}H_{44}N_2O_6S$. $1\frac{1}{4}H_2O$: C, 56.39; H, 9.17; N, 5.48; Found: C, 56.44; H, 8.75; N, 5.16.

EXAMPLE 2

Preparation of 4-hydroxy-5-[(2-carboxyethyl)thio]-6(Z)-nonadecenoic acid (Formula II) wherein m is 1, $R_1$ is hydrogen and $R_2$ is hydroxyl) as a mixture of the 4(R), 5(S) and the 4(S), 5(R) isomers A solution of 1.32 g (4.1 mmol) of 4,5-epoxy-6(Z)-nonadecenoic acid methyl ester and 1.46 g (12.2 mmol) of methyl-3-mercaptopropionate in 20 ml of methanol was treated with 1.62 g (16.1 mmol) of triethylamine in 10 ml of methanol under an argon atmosphere overnight. The reaction mixture was concentrated in vacuo and purification was carried out by chromatography on silica gel with hexane/ether (60/40) to give diester which contained some mono ester/lactone as evidenced by IR and tlc ($CH_2Cl_2$/hexane/acetone, 47/47/5).

A solution of this diester/lactone mixture (1.6 g, 3.6 mmol) in 30 ml of methanol was treated overnight with 1.43 g (36 mmol) of sodium hydroxide in 5 ml of water at room temperature, under an argon atmosphere. The reaction mixture was partly concentrated in vacuo, redissolved in 20 ml of water, and acidified with dilute phosphoric acid. The aqueous solution was extracted 3 times with 50 ml of ether, and the extracts were dried over magnesium sulfate, filtered and concentrated in vacuo to give white crystalline solid; m.p. 78°–80° C., Anal. calcd. for $C_{22}H_{40}O_5S$: C, 63.43, H, 9.68. Found: C, 63.11, H, 9.69.

EXAMPLE 3

Preparation of 5-[(3-carboxymethylamino-3-oxopropyl)thio]-4-hydroxy-6(Z)-nonadecenoic acid, [Formula (II) wherein m is 1, $R_1$ is hydrogen and $R_2$ is —$NHCH_2CO_2H$]

The above named compound was prepared by the general method of Example 2 using 3-carboxymethylamino-3-oxopropyl mercaptan, which in turn was prepared by the coupling reaction between 3,3'-dithiodipropionic acid and glycine methyl ester using DCC, followed by the reduction of the disulfide with tri-n-octyl phosphine in acetone/water 1:1 mixture. Product was obtained as an oil. Anal. calcd. for $C_{24}H_{43}NO_6S$: C, 60.85; H, 9.15, N, 2.95. Found: C, 60,65; H, 9.07; N, 2.89.

EXAMPLE 4

Preparation of 5-[(3-carboxymethyl-N-methylamino-3-oxopropyl)thio]-4-hydroxy-6(Z)-nonadecenoic acid, [Formula (II) where m is 1, $R_1$ is hydrogen and $R_2$ is

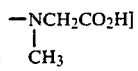

The above named compound was prepared by the general method of Example 2 using 3-carboxymethyl-N-methylamino-3-oxopropyl mercaptan. Mercaptan was prepared by coupling reaction between p-methoxy benzylthiopropionic acid and N-methyl glycine methyl ester in the presence of DCC, followed by treatment with HF at $-78°$ C. Product obtained had a melting point of 80°–82° C. Anal. calcd.: C, 61.57; H, 9.30; N, 2.87. Found: C, 61.55, H, 9.65; N, 3.02.

EXAMPLE 5

Preparation of 5-[(carboxymethyl)thio]-4-hydroxy-6(Z)-nonadecenoic acid [Formula (II) wherein m is 0; $R_1$ is hydrogen and $R_2$ is hydroxyl]

The above named compound was prepared by the general method of Example 2 using commercial methyl thioglycolate: mp 50°–52° C. Anal. calcd. for $C_{21}H_{38}O_5S$: C, 62.65; H, 9.51. Found: C, 62.74; H, 9.57.

EXAMPLE 6

Preparation of 5-[(3-carboxypropyl)thio]-4-hydroxy-6(Z)-nonadecenoic acid, [Formula (II) wherein m is 2; $R_1$ is hydrogen and $R_2$ is hydroxyl]

The above named compound was prepared by the general method of Example 2 using commercial 4-mercaptobutyric acid, mp 56°–58° C. Anal. calcd. for $C_{23}H_{42}O_5S \cdot \frac{1}{4}H_2O$: C, 63.48; H, 9.96. Found: C, 63.29; H, 9.75.

EXAMPLE 7

Preparation of 5-[[2-(aminocarbonyl)ethyl]thio]-4-hydroxy-6(Z)-nonadecenoic acid, [Formula (II) where m is 1; $R_1$ is hydrogen and $R_2$ is amino]

The above named compound was prepared by the general method of Example 2 using 2-(aminocarbonyl)ethyl mercaptan. Mercaptan was prepared by treatment of 3,3'-dithiodipropionyl iodide with concentrated ammonium hydroxide followed by the reduction of disulfide with tri-n-octylphosphine and acetone/water 1:1 mixture. Product obtained had a melting point of 84°–86° C. Anal. calcd. for $C_{22}H_{41}NO_4S$: C, 63.57; H, 9.94. Found: C, 63.56; H, 9.82.

EXAMPLE 8

Preparation of 4-hydroxy-5-[(2-amino-2-carboxyethyl)thio]-6(Z)-nonadecenoic acid [Formula (II) wherein m is 1; $R_1$ is amino and $R_2$ is hydroxyl] as the 4(R),5(S) isomer and the 4(R),5(S) isomer (a)

4-Hydroxy-5-[(2-trifluoroacetamido-2-carbomethoxyethyl)thio]-6(Z)-nonadecenoic acid, methyl ester and γ-lactone To the epoxide, methyl-4,5-epoxy-6(Z)-non-adecenoate (6) (0.9 g, 0.00277 mol) under argon at room temperature was added dropwise a solution of 1.2 g (0.00519 mol) of 2-trifluoroacetamido-2-carbomethoxyethylmercaptan in triethylamine (0.88 ml)/methanol (15 ml). The reaction mixture was stirred at room temperature for 30 hours, concentrated in vacuo and then filtered through a silica gel bed, eluting the product mixture with chloroform. The chloroform wash was concentrated to give a mixture of the above-noted methyl ester and γ-lactone.

(b)

4-Hydroxy-5-[(2-trifluoroacetamido-2-carbomethoxyethyl)thio]-6(Z)-nonadecenoic acid, γ-lactone The crude mixture (2 g) of the methyl ester and γ-lactone from Example 8(a) in 75 ml of toluene was heated to 80° C. in the presence of 27 mg of p-toluenesulfonic acid for 20 minutes. The reaction mixture was then concentrated in vacuo and the residue was taken up in methylene chloride, washed with 5% sodium bicarbonate solution, dried with brine and anhydrous sodium sulfate and then concentrated in vacuo. The resulting crude oil was applied to the Water's Preparative HPLC (2 Prepak silica columns, eluting with 25% ethyl acetate in hexane) to give the desired products as the 4(R), 5(S) isomer and the 4(S), 5(R) isomer. Each individual diasteromer was purified further on a silica "flash" column, eluting with 30% ethyl acetate in hexane.

(c)

4(R)-Hydroxy-5(S)-[(2-amino-2-carboxyethyl)thio]-6(Z)-nonadecenoic acid, sodium salt A partial suspension of 4(R), 5(S) isomer of the γ-lactone of Example 8(b) (0.3 g, 0.00057 mol) in aqueous sodium hydroxide (0.205 g, 0.004 mol in 13 ml water) was stirred for 24 hours at room temperature. The pH of the reaction mixture was then adjusted to 3.5 with concentrated hydrochloric acid to give the desired product: mp 168°–170° C. Anal. calcd. for $C_{22}H_{41}NO_5S \cdot 1Na$ ($-1H$): C, 58.12; H, 8.87; N, 3.08. Found: C, 57.99; H, 8.85; N, 3.70.

(d)

4(S)-Hydroxy-5(R)-[(2-amino-2-carboxyethyl)thio]-6(Z)-nonadecenoic acid, sodium salt The reaction was carried out as described in Example 8(c), to give the desired product: mp 159°–161° C. Anal. Calcd. for $C_{22}H_{41}NO_5S \cdot 1.5\ Na$ ($--1.5\ H$): C, 56.69; H, 8.54; N, 3.01. Found: C, 56.40; H, 8.19; N, 3.33.

EXAMPLE 9

Preparation of
5[-(2-amino-3-carboxamidomethylamino-3-oxopropyl)-thio]-4-hydroxy-6(Z)-nonadecenoic acid [Formula (II) wherein m is 1; $R_1$ is amino and $R_2$ is —NHCH$_2$CONH$_2$]

(a)

4(R)-Hydroxy-5(S)-[(2-trifluoroacetamido-3-carbamoylmethylamino-3-oxopropyl)thio]-6(Z)-nonadecenoic acid, γ-lactone-4(R)-hydroxy-5(S)-[(2-trifluoroacetamido-3-carbamoylmethylamino-3-oxopropyl)thio]-6(Z)-nonadecenamide A mixture of lactone methyl ester prepared according to Example 1(g) (0.41 g, 0.7 mmol) in 10 ml of dimethoxyethane, 10 ml of methanol, and 20 ml of concentrated ammonium hydroxide solution was stirred at 0° C. for 2 hours. The mixture was neutralized in the cold with concentrated hydrochloric acid to pH 7.5. The crude product was partitioned into methylene chloride. The aqueous phase was further extracted 2×40 ml methylene chloride. The combined extracts were washed with saturated sodium chloride solution, dried over sodium sulfate, and evaporated to give oil residue. Flash column chromatography (silica gel, 1.5"×6"", 3% CH$_3$OH/CHCl$_3$, 25 ml fraction) gave the desired products. The 6(Z)-nonadecenamide had the following properties: mp 143°–5° C.; Anal. calcd. for C$_{26}$H$_{45}$F$_3$N$_4$O$_5$S: C, 53.59; H, 7.78; N, 9.61. Found: C, 53.86; H, 7.52; N, 9.83.

(b)

4(R)-Hydroxy-5(S)-[(2-amino-3-carbamoylmethylamino-3-oxopropylthio)-6(Z)-nonadecenoic acid A mixture of 120 mg (0.2 mmol) of the γ-lactone of Example 9(a) in 5 ml of 0.2M sodium hydroxide solution was stirred at room temperature for 18 hours. The mixture was acidified to pH 3 by adding a concentrated hydrochloric acid solution in ice-bath. The resulting precipitates were filtered and washed quickly with cold water and dried at 56° C. for 24 hours to give the desired product, mp. 143°–5° C.; Anal. calcd.: C, 57.51; H, 9.35; N, 8.38; Found C, 57.50; H, 9.42; N, 6.72.

EXAMPLE 10

Preparation of
3-hydroxy-4-[(2-carboxyethyl)thio]-5(Z)-octadecenoic acid [Formula (III) wherein m is 1; X is hydroxyl, $R_1$ is hydrogen and $R_2$ is hydroxyl]

(a)

Heptadec-2(E),4(Z)-dienyl tetrahydropyranyl ether 10(a)(1)

Heptadec-2(E),4(E)-dienyl tetrahydropranyl ether 10(a)(2)

Tridecyltriphenyl phosphonium bromide (189 g, 0.36 mole) was dissolved in 900 ml of tetrahydrofuran and cooled to 0° C. in an ice-salt bath while stirring under argon. A 2.2N solution of n-butyllithium in hexane (250 ml, 0.36 mole) was added dropwise over a period of 30 minutes. The mixture was stirred for an additional 20 minutes and then cooled to −70° C. in a dry ice-acetone bath. The 4-hydroxybut-2(E)-ene-1-al tetrahydropyranyl ether (51 g, 0.3 mole) in 225 ml of tetrahydrofuran was added dropwise over a period of 35 minutes and the mixture stirred for an additional hour at −70° C. The mixture was then poured into 6.25 liters of ether and stirred for 20 minutes. The resulting mixture was filtered through glass fiber filter paper. The filtrate was evaporated and the residue triturated with hexane, filtered, evaporated, and flash chromatographed to give a ~3:1 mixture of 10(a)(1): 10(a)(2).

(b)

Heptadec-2(E),4(Z)-dien-1-ol 10(b)(1)

Heptadec-2(E),4(E)-dien-1-ol 10(b)(2)

The mixture of compounds 10(a)(1) and 10(a)(2) (80 g, 0.24 mole) was dissolved in 3 liters of methanol and the pyridinium p-toluenesulfonate (3 g, 0.012 mole) was added to the mixture stirring under argon at room temperature. The progress of the reaction was monitored by tlc. When the reaction was complete the solvent was evaporated and the reaction flash chromatographed on 500 grams of silica gel eluted with 10% ethyl acetate in hexane to give 52 grams (87%) of a ~3:1 mixture of 10(b)(1):10(b)(2). Separation of 10(b)(1) from 10(b)(2) was accomplished by careful chromatography on silica gel. Compound 10(b)(1) mp 34°–37° C. Compound 10(b)(2) mp 51°–55° C.

(c)

Trans-2,3-epoxy-heptadec-4(Z)-ene-1-ol 10(c)

Compound 10(b)(1) (2.52 g, 10 mmol) was dissolved in 100 ml of methylene chloride stirring at room temperature under argon. A 0.5N solution of sodium bicarbonate (30 ml) was added. The 85% m-chloroperbenzoic acid (2.03 g, 10 mmol) was added slowly in small portions. The mixture was stirred for 1.5 hours after the addition was complete. The phases were separated and the aqueous phase washed with methylene chloride. The combined organic phases were dried over anhydrous sodium sulfate filtered and evaporated. The residue was flash chromatographed on 100 grams of silica gel eluted with 10-20% ethyl acetate-hexane to give compound 10(c).

(d)

Methyl 3-(1,2-dihydroxyheptadec-4(Z)-enyl)thiopropionate 10(d)

Compound 10(c) (7.2 g, 26.9 mmol) was dissolved in 40.2 ml of methanol containing 2% triethylamine. This solution was stirred at room temperature under argon and a solution of methyl 3-mercaptopropionate (4.92 ml, 44.4 mmol) and triethylamine (11.16 ml, 80.2 mmol) in 40.2 ml of methanol was added dropwise over a period of 15 minutes. The mixture was stirred for 5 hours at room temperature and then placed in the refrigerator overnight. The solvents were evaporated and the residue flash chromatographed on 500 grams of silica gel eluted with 10-50% ethyl acetate in hexane to give compound 10(d), mp. 33°–36°.

(e)

2-[(2-Carbomethoxyethyl)thio]hexadec-3(Z)-enal 10(e)

Compound 10(d) (2 g, 5.15 mmol) was dissolved in 10 ml of diethyl ether and stirred in a room temperature water bath. A saturated solution (100 ml) of periodic acid in diethyl ether was added in a single portion. The resulting mixture was stirred for two minutes and then immediately flash chromatographed on 150 g of silica gel with 10% ethylacetate in hexane to give compound 10(e).

(f)

Methyl 3-hydroxy-4-[(2-carbomethoxyethyl)thio]octadec-5(Z)-enoate 10(f)

A dry flask sealed with a septum and maintained under an argon atmosphere was charged with 4.5 ml of hexane and cooled in an ice bath. A 2.2M solution of n-BuLi (1.03 ml, 2.25 mmol) was added followed by the dropwise addition of diisopropyl amine (0.315 ml, 2.25 mmol). The solution was stirred at 0° C. for 10 minutes and then cooled to −78° C. in a dry ice-acetone bath for 15 minutes. A solution of methyl acetate (0.18 ml, 2.25 mmol) in 1.5 ml hexane was added over a period of 1 minute and the mixture stirred at −78° C. for an additional minute. The mixture at this time was almost clear. Compound 10(e) (750 mg, 2.1 mmol) in 1.5 ml of hexane was added over a period of 1 minute resulting in a clear yellow solution which was stirred at −78° C. for an additional 15 minutes. The reaction mixture was then flash chromatographed on 100 grams of silica gel eluted with 15% ethyl acetate in hexane to give compound 10(f).

(g)

3-Hydroxy-4-[(2-carboxyethyl)thio]-5(Z)-octadecenoic acid

Compound 10(f) (0.2 g, 0.46 mmol) was dissolved in 5 ml of methanol and stirred under an argon atmosphere at 0° C. A 1N solution of sodium hydroxide (2 ml, 2 mmol) was added dropwise over a period of 0.5 minute. The ice bath was removed and the reaction allowed to warm to room temperature for 2 hours. Most of the methanol was evaporated and the aqueous residue was cooled in an ice bath and acidified with dilute hydrochloric acid. The aqueous phase was extracted twice with diethyl ether. The combined ether extracts were dried over anhydrous sodium sulfate, filtered, and evaporated to give crude product. This was recrystallized from diethyl ether-hexane to give the desired compound, mp 88°–97° C. Anal. Calcd. C: 62.65; H: 9.51; S: 7.96; Found C: 62.32; H: 9.38; and S: 8.10.

The following compounds are prepared by the general method of Example 10 by employing the appropriate thiol containing compound for methyl-3-mercaptoproprionate:

3-hydroxy-4-[(carboxymethyl)thio]-5(Z)-octadecenoic acid;
3-hydroxy-4-[(3-carboxypropyl)thio]-5(Z)-octadecenoic acid;
3-hydroxy-4-[(3-carboxymethylamino-3-oxopropyl)thio]-5(Z)-octadecenoic acid;
3-hydroxy-4-[(2-amino-3-carboxymethylamino-3-oxopropyl)thio]-5(Z)-octadecenoic acid;
3-hydroxy-4-[[(aminocarbonyl)ethyl]thio]-5(Z)-octadecenoic acid; and
3-hydroxy-4-[(2-amino-2-carboxyethyl)thio]-5(Z)-octadecenoic acid.

EXAMPLE 11

Preparation of 5-[(2-carboxyethyl)thio]-6(Z)-non-adecenoic acid [Formula (IV) wherein n is 2; m is 1; p is 11; $R_1$ is hydrogen and $R_2$ is hydroxyl]

(a)

2-Bromo-5-carbomethoxypentanoic acid 11(a)

To a solution of 30 gm (0.187M) of 5-carbomethoxypentanoic acid in 250 ml of chloroform was added 90 gm of thionyl chloride. The mixture was refluxed for 2 hours, cooled and the solvent removed under vacuum. The residue was redissolved in 200 ml of carbon tetrachloride, 40 gm (0.225M) of N-bromosuccinimide was added, the mixture heated to reflux, eight drops of a HBr/acetic acid mixture added, and the reaction refluxed for 3 hours. After cooling, the mixture was filtered and evaporated to dryness. The residue was dissolved in 250 ml of acetone to which was added dropwise 200 ml of a freshly prepared 5% sodium bicarbonate solution. After stirring for 15 minutes during which time the pH was constantly adjusted to pH 9 with sodium bicarbonate the mixture was acidified with dilute HCl, to a pH 1.0, concentrated in vacuum, and extracted with chloroform. The organic phase was extracted with dilute bicarbonate solution, acidified and reextracted with chloroform. The extract was dried over MgSO$_4$, filtered and evaporated to dryness to afford the desired compound as a viscous oil.

(b)

5-Carbomethoxy-2-[(methoxycarbonylpropyl)thio]pentanoic acid 11(b)

A mixture of 42 gm (0.175M) of 11(a), 50.68 g (0.42M) of methyl-3-mercaptoproprionate and 147 ml (1.05M) of triethylamine in 250 ml of methanol was refluxed for two hours, cooled and concentrated in vacuum. The residue was dissolved in ethyl acetate and extracted with 5% sodium bicarbonate. The aqueous extract was acidified with 3N HCl, extracted with chloroform, the extract dried over MgSO$_4$, filtered and evaporated to dryness to afford the desired compound.

(c)

5-Carbomethoxy-2[(methoxycarbonylpropyl)thio]pentanol 11(c)

A solution of 11(b) (40 g, 0.142M) in THF (200 ml) was placed in a methanol-ice (−10° C.) bath. The contents were permitted to cool for 20 minutes at which time 12.57 g (0.156M) of borane-methyl sulfide complex was added slowly over a period of 50 minutes, followed by refluxing for 30 minutes. Acetic acid (10 ml) was then added and excess THF evaporated. The reaction mixture was dissolved in ethyl acetate (300 ml), washed with 5% sodium bicarbonate, dried over MgSO$_4$ and filtered. Evaporation afforded the crude alcohol.

(d)

5-Carbomethoxy-2[(methoxycarbonylpropyl)thio]pentanal 11(d)

Methylene chloride (10 ml.) and Me$_2$SO (1.78 g, 0.23M) were combined and cooled to −65° C. TFAA (1.73 g, 0.015M) was added dropwise to the cold solution, at which time a white precipitate formed. After 5 minutes at −65° C., a solution of 11(c) (2.0 g, 7.58 mmol) in $CH_2Cl_2$ (5 ml) was added dropwise while maintaining the reaction mixture at $-65°$ C. The mixture was then stirred at $-65°$ C. for 30 minutes, followed by addition of TEA (2.30 g, 0.023M) dropwise. A temperature below $-60°$ C. was maintained until addition of TEA was complete. The bath was then removed and the reaction permitted to warm to room temperature. The mixture was diluted with $CH_2Cl_2$, washed with 3N HCL, $H_2O$, twice with 5% $NAHCO_3$ and once with brine. The organic phase was then dried over $MgSO_4$, filtered and evaporated to dryness to afford the crude aldehyde.

(e)

Methyl-5-[(2-carbomethoxyethyl)thio]-6(Z)-nonadecanoate 11(e)

A mixture of tridecyltriphenyl phosphonium bromide (1.76 g, 3.35M) and THF (20 ml) was permitted to stir for 5 minutes at room temperature. The solution was then cooled to $-68°$ C. and stirred for an additional 10 minutes. At which time N-butyllithium (3.05 mmol) was slowly added while maintaining a $-65°$ C. temperature. Following stirring for 10 minutes at $-68°$ C. the reaction mixture was stirred for an additional 10 minutes at $-10°$ C. Upon recooling to $-68°$ C., (0.918 g, 3.50 mmol) of 11(d) was dissolved in THF (10 ml) and slowly added. The reaction was stirred for one hour at $-68°$ C. followed by removal of the bath in order to warm the mixture to room temperature. THF was then evaporated and the residue dissolved in ethyl acetate, which as washed with 3N HCL, water and twice with 5% $NAHCO_3$. The extract was dried over $MgSO_4$, filtered and evaporated to dryness. The product was flash chromatographed with 91% hexane: 9% EtOAc to provide the nonadecanoate.

(f)

5-[(2-Carboxyethyl)thio]-6(Z)-nonadecanoic acid

Potassium carbonate (0.81 g, 5.84 mmol) was dissolved in $H_2O$ (10 ml), to which was added methanol (5 ml). The solution was stirred for 2 minutes at room temperature, followed by the addition of 11(e) (100 mg; 0.234 mmol) in MeOH (24 ml). The mixture was permitted to stir overnight at room temperature, after which time excess MeOH was evaporated and the remaining aqueous phase was then washed with ethyl acetate, acidified to a pH=1.0 with 3N HCL and extracted twice with ethyl acetate, the extract was dried over $MgSO_4$, filtered and evaporated to an oil. The product was recrystallized from ether-petroleum ether and cooled for one hour to afford the nonadecanoic acid as a white crystalline solid (mp 53°-54° C.).

The following compounds are prepared by the general method of Example 11 by employing the appropriate thiol containing compound for methyl-3-mercaptoproprionate:

5-[(carboxymethyl)thio]-6(Z)-nonadecenoic acid;
5-[(3-carboxypropyl)thio]-6(Z)-nondecenoic acid;
5-[(3-carboxymethylamino-3-oxopropyl)thio]-6(Z)-nonadecenoic acid;
5-[(2-amino-3-carboxymethylamino-3-oxopropyl)thio]-6(Z)-nonadecenoic acid;
5-[[(aminocarbonyl)ethyl]thio]-6(Z)-nonadecenoic acid; and
5-[(2-amino-2-carboxyethyl)thio]-6(Z)-nonadecenoic acid.

EXAMPLE 12

Preparation of 5-[(2-carboxyethyl)thio]-4-hydroxy-6(Z)-nonadecenamide, [Formula (V) where m is 1, $R_1$ is hydrogen and $R_2$ is hydroxyl]

The above named compound was prepared by treatment of the compound of Example 2 with 1% solution of trifluoroacetic anhydride in $CH_2Cl_2$ for 2 hours at room temperature, followed by treatment with $NH_3$ in methanol solution at 0° C. for 0.5 hour and room temperature overnight. Product was obtained as a crystalline solid mp 82°-85° C.; Anal. Calcd. for $C_{22}H_{41}NO_4S$ 0.3M $NH_3$: C, 62.77; H, 9.89; N, 4.33. Found: C, 62.67, 62.98; H, 9.92, 9.78; N, 3.98, 4.00.

EXAMPLE 13

Preparation of 5-[(3-carboxymethylamino-3-oxopropyl)thio]-4-hydroxy-6(Z)-nonadecenamide [Formula (V) where m is 1, $R_1$ is amino and $R_2$ is $-NHCH_2CO_2H$]

A mixture of 0.9 g (1.4 mmol) of compounds of Example 1(g) in 100 ml of 3.8% anhydrous ammonia in ethanol solution was stirred at room temperature for 2 days. The reaction mixture was concentrated to dryness. The residue was azeotroped with methylene chloride to give 0.9 g of off-white powder. The hydroscopic material was dissolved in 10% NaOH solution (5 ml) and chromatographed on a 3-cm-by-9-cm column of XAD-7 resin. After washing with $H_2O$ (100 ml), the column was eluted with aqueous methanol solution (1:1) taking 20 ml per fraction. Fraction 13 was collected to give the desired product as a white amorphous powder, mp 195°-8° C. Anal. Calcd. for $C_{24}H_{44}N_3O_5S$ Na(H) $2H_2O$: C, 52.82; H, 8.87; N, 7.70. Found: C, 52.65; H, 8.15; N, 7.72.

EXAMPLE 14

Preparation of 4-hydroxy-5-[(2-carboxyethyl)thio](Z)-hepadecenoic acid [Formula (VI) wherein m is 1, $R_1$ is hydrogen and $R_2$ is hydroxyl]

The above named compound was prepared by the general method of Example 2 using 4,5-epoxy-6(Z)-heptadecenoic acid methyl ester, which was obtained by employing the general method of Example 1(e) using undecyltriphenyl phosphonium bromide. The product obtained had a melting point of 78.5°-80° C. Anal. calcd.: C, 61.82; H, 9.34; S, 8.25. Found C, 61.82; H, 9.10; S, 8.42.

The following compounds are prepared by the general method of Example 14 by employing the appropriate thiol containing compound for methyl-3-mercaptopropionate:

4-hydroxy-5-[(carboxymethyl)thio]-6(Z)-heptadecenoic acid;
4-hydroxy-5-[(3-carboxypropyl)thio]-6(Z)-heptadecenoic acid;
4-hydroxy-5-[(3-carboxymethylamino-3-oxopropyl)thio]-6(Z)-heptadecenoic acid;
4-hydroxy-5-[(2-amino-3-carboxymethylamino-3-oxopropyl)thio]-6(Z)-heptadecenoic acid;
4-hydroxy-5-[[(aminocarbonyl)ethyl]thio]-6(Z)-heptadecenoic acid; and
4-hydroxy-5-[(2-amino-2-carboxyethyl)thio]-6(Z)-heptadecenoic acid.

EXAMPLE 15

Preparation of
4-Hydroxy-5-[(2-carboxyethyl)thio-6(Z)-heneicosenoic acid [Formula (VII) wherein m is 1, $R_1$ is hydrogen and $R_2$ is hydroxyl]

The above named compound was prepared by the general method of Example 2 using 4,5-epoxy-6(Z)-heneicosenoic acid methyl ester, which was obtained by employing the general method of Example 1(e) using pentadecyltriphenyl phosphonium bromide. The product obtained had a melting point 59°–61° C. Anal. calcd.: C, 64.82; H, 9.97; S, 7.21. Found C, 65.16; H, 10.07; S, 7.36.

The following compounds are prepared by the general method of Example 15 by employing the appropriate thio containing compound for methyl-3-mercaptopropionate:

4-hydroxy-5-[(carboxymethyl)thio]-6(Z)-heneicosenoic acid;
4-hydroxy-5-[(3-carboxypropyl)thio]-6(Z)-heneicosenoic acid;
4-hydroxy-5-[(3-carboxymethylamino-3-oxopropyl)thio]-6(Z)-heneicosenoic acid;
4-hydroxy-5-[(2-amino-3-carboxymethylamino-3-oxopropyl)thio]-6(Z)-heneicosenoic acid;
4-hydroxy-5-[[(aminocarbonyl)ethyl]thio]-6(Z)-heneicosenoic acid; and
4-hydroxy-5-[(2-amino-2-carboxyethyl)thio]-6(Z)-heneicosenoic acid.

EXAMPLE 16

Preparation of
4-[(2-carboxyethyl)thio]-5(Z)-octadecenoic acid
[Formula (III) wherein m is 1; X is hydrogen; $R_1$ is hydrogen and $R_2$ is hydroxyl]

(a)

Methyl-4-bromo-4-carboxybutanoate 16(a)

Methyl-4-(chloroformyl)butyrate (30.0 g, 0.182M) was charged to a flask, along with 200 ml of CCl$_4$. To this solution N-bromosuccinimide (40.0 g, 0.219M) was added. The reaction mixture was heated to reflux and seven drops of 47% aqueous HBr was added, reflux conditions continued for approximately 2 hours. Following cooling to room temperature, the reaction was filtered and evaporated to dryness. The residue was then placed in the refrigerator overnight. The residue was dissolved in 250 ml of acetone, to which is added saturated sodium bicarbonate during which time the ph was adjusted to nine. With dilute HCl the mixture was then acidified to a pH=1.0, concentrated and extracted with chloroform. The extract was dried over MgSO$_4$, filtered and evaporated to dryness to afford the desired compound as an oil.

(b)

Methyl-4-[(2-carbomethoxyethyl)thio]-4-carboxy butanoate 16(b)

To a stirred solution of 29.0 g (0.24M) of methyl-3-mercaptopropionate and 61.0 g (0.60M) of triethylamine in 200 ml of methanol was added 22.5 (0.10M) of 16(a) under argon. After stirring at room temperature for ten minutes, the reaction was heated to reflux for one and a half hours, cooled to room temperature and concentrated in a vacuum. The residue was then diluted with ethyl acetate, extracted with 5% sodum bicarbonate, acidified to pH 1.6 with dilute HCl and reextracted into chloroform several times. Organic extracts were then combined, dried over MgSO$_4$, filtered and evaporated to dryness to afford the desired compound.

(c)

Methyl-4-[(2-carbomethoxyethyl)thio]-5-hydroxy pentanoate 16(c)

A solution of 16(b) (21.4 g; 0.08M) in THF (175 ml) was cooled to −10° C. in a methanol-ice bath. The contents were premitted to cool for 10 minutes at which time borane methyl sulfide complex (7.2 g; 0.09M) was added slowly. Following addition reaction was warmed to room temperature and then refluxed for approximately 15 minutes. After cooling acetic acid (6 ml) was added and execess THF evaporated. The reaction mixture was dissolved in ethyl acetate, washed with 5% sodium bicarbonate, dried over MgSO$_4$, filtered, evaporated to dryness to afford the crude alcohol. This material was then flash chromatographed using a 60% ethyl acetate in hexane system to yield a purer product.

(d)

Methyl-4-[(2-carbomethoxyethyl)thio]-4-formyl butanoate 16(d)

Methylene chloride (20 ml) and Me$_2$SO (1.14 ml; 0.016M) were combined and cooled to −65° C. TFAA (0.91 ml; 0.012M) was added dropwise to the cold solution at which time a white precipitate formed. After 5 minutes a solution of 16(c) (2.0 g; 0.008M) in methylene chloride (3 ml) was added dropwise while maintaining the temperature at −65° C. The reaction mixture was then stirred for thirty minutes followed by addition of TEA (3.1 ml; 0.022M) dropwise. The reaction mixture was stirred for an additional thirty minutes at −65° C., at which it was diluted with methylene chloride, washed with dilute HCl, water and then twice with 5% sodium bicarbonate. The organic phase was then dried over MgSO$_4$, filtered and evaporated to dryness to afford the crude aldehyde. This material was flash chromatographed using 50% ethyl acetate in hexane resulting in purer product.

(e)

Methyl-4-[(2-carbomethoxyethyl)thio]-5(Z)-octadecenoate 16(e)

A mixture of tridecyltriphenyl phosphonium bromide (1.27 g; 2.4 mmol) and THF (20 ml) was allowed to stir for 3 minutes at room temperature. The solution was then cooled to −68° C., at which time n-butyllithium (1.05 ml; 2.4 mmol) was added slowly while maintaining a reaction temperature less than −65° C. Following stirring at −68° C. the reaction was permitted to warm to −10° C. for approximately 10 minutes. Upon recooling to −68° C., (0.05 g; 2.0 mmol) of 16(d) was dissolved in THF (10 ml) and slowly added. Te reaction was stirred for one hour at −68° C. followed by removal of the bath. Product was then triturated into hexane and also into ether, hexane and ether fractions were combined, evaporated to dryness and the remaining residue was flash chromatographed affording to desired octadecenoate.

(f)

4-[(2-Carboxyethyl)thio]-5(Z)-octadecenoic acid (f)

(319 mg; 0.826 mmol) of 16(e) was dissolved in methanol (7.5 ml) and permitted to stir under argon at 0° C. A 1N solution of sodium hydroxide (3.1 ml; 3.08 mmol) was added dropwise. The ice bath was then removed and the reaction allowed to warm to room temperature for approximately three hours. After which it was placed in the refrigerator and stored overnight. Most of the methanol was then evaporated and the aqueous residue was cooled in an ice bath followed by acidification with dilute HCL. The aqueous phase was extracted twice with diethyl ether. The ether extracts were then combined and dried over magnesium sulfate, filtered and evaporated to give crude product. This was then recrystallized from diethyl ether-hexane to afford the final product, mp 81° C.; Anal. Calcd C: 65.24; H: 9.91; S: 8.29; Found C: 65.50; H: 10.05; S: 8.61.

The following compounds are prepared by the general method of Example 16 by employing the appropriate thiol containing compound for methyl-3-mercaptoproprionate:

4-[(carboxymethyl)thio]-5(Z)-octadecenoic acid;
4-[(3-carboxypropyl)thio]-5(Z)-octadecenoic acid;
4-[(3-carboxymethylamino-3-oxopropyl)thio]-5(Z)-octadecenoic acid;
4-[(2-amino-3-carboxymethylamino-3-oxopropyl)thio]-5(Z)-octadecenoic acid;
4-[[(aminocarbonyl)ethyl]thio]-5(Z)-octadecenoic acid; and
4-[(2-amino-2-carboxyethyl)thio]-5(Z)-octadecenoic acid.

EXAMPLE 17

As a specific embodiment of a composition of this invention, an active ingredient, such as the compound of Example 1(i), is dissolved in sterile water at a concentration of 0.5 percent and aerosolized from a nebulizer operating at an air flow adjusted to deliver the desired aerosolized weight of drug.

EXAMPLE 18

As an additional specific embodiment of a composition of this invention, an active ingredient, such as the compound of Example 2, is admixed with mannitol at a concentration of 1.0 percent and administered from a powder inhalation device adjusted to deliver the desired weight of drug.

What is claimed is:

1. A compound represented by the formula (I)

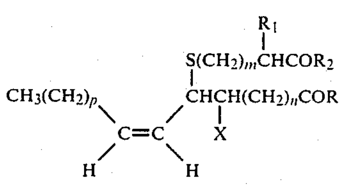

(I)

wherein n is 1 or 2; m is 0, 1, or 2; p is 9, 10, 11, 12 or 13; X is hydrogen or hydroxyl; R is hydroxyl or amino; $R_1$ is hydrogen, amino or 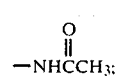 $R_2$ is hydroxyl, amino, 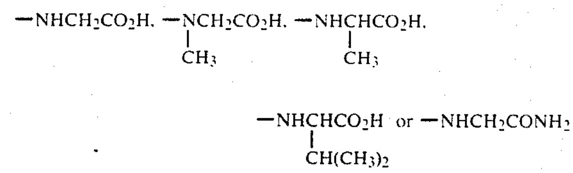 or with the proviso that m is 0, $R_1$ is hydrogen or a pharmaceutically acceptable salt thereof.

2. A compound of claim 1 wherein n is 2 and p is 11.

3. A compound of claim 2 wherein R is hydroxyl and X is hydroxyl represented by the formula (II)

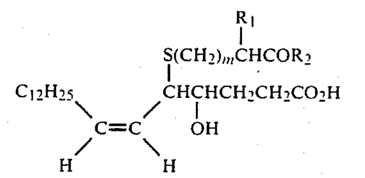

(II)

wherein m is 0, 1 or 2; $R_1$ is hydrogen, amino or 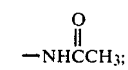 and $R_2$ is hydroxyl, amino, 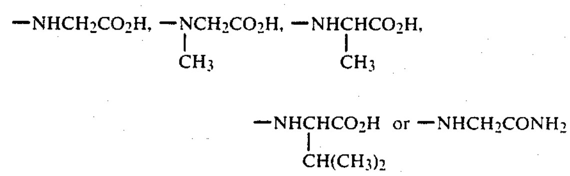 or with the proviso that when m is 0, $R_1$ is hydrogen.

4. A compound of claim 3 wherein m is 1, $R_1$ is hydrogen and $R_2$ is 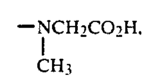 designated 5[(3-carboxy-methyl-N-methylamino-3-oxopropyl)thio]-4-hydroxy-6(Z)-nonadecenoic acid.

5. A compound of claim 3 wherein m is 0, $R_1$ is hydrogen and $R_2$ is hydroxyl, designated 4-hydroxy-5-[(2-carboxymethyl)thio]-6(Z)-nonadecenoic acid.

6. A compound of claim 3 wherein m is 1, $R_1$ is hydrogen and $R_2$ is amino, designated 5-[[(2-aminocarboxyl)ethyl]thio]-4-hydroxy-6(Z)-nonadecenoic acid.

7. A compound of claim 3 wherein m is 2, $R_1$ is hydrogen and $R_2$ is hydroxyl, designated 4-hydroxy-5-[(3-carboxypropyl)thio]-6(Z)-nonadecenoic acid.

8. A compound of claim 1 wherein n is 1 and p is 11.

9. A compound of claim 8 wherein R is hydroxyl represented by the formula (III)

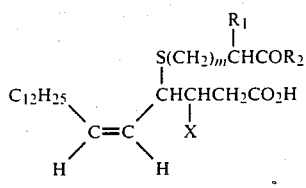 (III)

wherein m is 0, 1 or 2; X is hydrogen or hydroxyl; $R_1$ is hydrogen, amino or

and $R_2$ is hydroxyl, amino

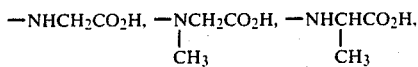

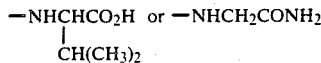

with the proviso that when m is 0 $R_1$ is hydrogen.

10. A compound of claim 9 wherein m is 1, X is hydroxyl; $R_1$ is hydrogen and $R_2$ is hydroxyl, designated 3-hydroxy-4-[(2-carboxyethyl)thio]-5(Z)-octadecenoic acid.

11. A compound of claim 1 wherein n is 2 and p is 9.

12. A compound of claim 11 wherein R is hydroxyl and X is hydroxyl.

13. A compound of claim 12 wherein m is 1, R is hydrogen and $R_2$ is hydroxyl, designated 4-hydroxy-5-[(2-carboxyethyl)thio]-6(Z)-heptadecenoic acid.

14. A compound of claim 1 wherein n is 2 and p is 13.

15. A compound of claim 14 wherein R is hydroxyl and X is hydroxyl.

16. A compound of claim 15 wherein m is 1, $R_1$ is hydrogen and $R_2$ is hydroxyl, designated 4-hydroxy-5-[(2-carboxyethyl)thio]-6(Z)-heneicosenoic acid.

17. A pharmaceutical composition for inhibiting the effects of leukotriene in subjects in need of such inhibition comprising a pharmaceutical carrier of diluent and a nontoxic amount sufficient to produce said inhibition of a compound of claim 1.

18. A pharmaceutical composition according to claim 17 in a form suitable for administration by inhalation.

19. A pharmaceutical composition according to claim 18 in the form of an aerosol formulation.

20. A pharmaceutical composition according to claim 17 in a form suitable for administration by parenteral administration.

21. A pharmaceutical composition according to claim 20 in the form of a sterile solution.

22. A compound represented by the formula:

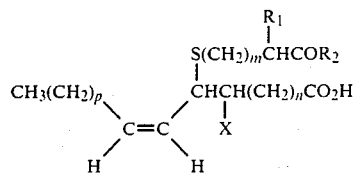

wherein n is 1 or 2; m is 0, 1 or 2; p is 9, 10, 11, 12 or 13; X is hydrogen or hydroxyl; $R_1$ is hydrogen or amino; and $R_2$ is hydroxyl or $NHCH_2CO_2H$, with the proviso that when m is 0, $R_1$ is hydrogen, or a pharmaceutically acceptable salt thereof.

23. A compound of claim 22 wherein X is hydroxyl.

24. A compound of claim 23 wherein m is 1 and n is 2.

25. A compound of claim 24 wherein m is 1, $R_1$ is hydrogen and $R_2$ is hydroxyl, designated 4-hydroxy-5-[(2-carboxyethyl)thio]-6(Z)-nonadecenoic acid.

26. A compound of claim 24 wherein m is 1, $R_1$ is hydrogen and $R_2$ is $-NHCH_2CO_2H$, designated 5-[(3-carboxymethylamino-3-oxopropyl)thio]-4-hydroxy-6(Z)-nonadecenoic acid.

27. A compound of claim 24 wherein m is 1, $R_1$ is amino and $R_2$ is $-NHCH_2CO_2H$, designated 5-[(2-amino-3-carboxymethylamino-3-oxopropyl)thio]-4-hydroxy-6(Z)-nonadecenoic acid.

28. A compound of claim 27 which is the 4(R),5(S) isomer designated 5(S)-[(2-amino-3-carboxymethylamino-3-oxopropyl)thio]-4(R)-hydroxy-6(Z)-nonadecenoic acid.

29. A compound of claim 27 which is the 4(S),5(R) isomer designated 5(R)-[(2-amino-3-carboxymethylamino-3-oxopropyl)thio]-4(S)-hydroxy-6(Z)-nonadecenoic acid.

30. A compound of claim 24 wherein m is 1, $R_1$ is amino and $R_2$ is hydroxyl, designated 4-hydroxy-5-[(2-amino-2-carboxyethyl)thio]-6(Z)-nonadecenoic acid.

31. A compound of claim 30 which is the 4(R),5(S) isomer designated 4(R)-hydroxy-5(S)-[(2-amino-2-carboxyethyl)thio]-6(Z)-nonadecenoic acid.

32. A compound of claim 30 which is the 4(S),5(R) isomer designated 4(S)-hydroxy-5(R)-[(2-amino-2-carboxyethyl)thio]-6(Z)-nonadecenoic acid.

* * * * *